United States Patent
Freed et al.

(10) Patent No.: US 11,903,741 B2
(45) Date of Patent: *Feb. 20, 2024

(54) SHOCKABLE HEART RHYTHM CLASSIFIER FOR DEFIBRILLATORS

(71) Applicant: Avive Solutions, Inc., San Francisco, CA (US)

(72) Inventors: Benjamin C. Freed, Frederick, MD (US); David P. Walter, III, Cambridge, MA (US)

(73) Assignee: Avive Solutions, Inc., Brisbane, CA (US)

( * ) Notice: Subject to any disclaimer, the term of this patent is extended or adjusted under 35 U.S.C. 154(b) by 365 days.

This patent is subject to a terminal disclaimer.

(21) Appl. No.: 17/364,575

(22) Filed: Jun. 30, 2021

(65) Prior Publication Data

US 2021/0321926 A1    Oct. 21, 2021

Related U.S. Application Data

(63) Continuation of application No. 16/568,030, filed on Sep. 11, 2019, now Pat. No. 11,089,989.
(Continued)

(51) Int. Cl.
*A61B 5/00*   (2006.01)
*A61N 1/39*   (2006.01)
(Continued)

(52) U.S. Cl.
CPC ............ *A61B 5/7267* (2013.01); *A61B 5/346* (2021.01); *A61B 5/361* (2021.01); *A61B 5/7264* (2013.01);
(Continued)

(58) Field of Classification Search
CPC ......... A61B 5/316; A61B 5/346; A61B 5/361; A61B 5/366; A61B 5/7203; A61B 5/7221;
(Continued)

(56) References Cited

U.S. PATENT DOCUMENTS 5,092,343 A   3/1992 Spitzer et al.
5,280,792 A   1/1994 Leong et al.
(Continued)

FOREIGN PATENT DOCUMENTS

CN   106805965   6/2017
KR   10-2013-0050707   5/2013
(Continued)

OTHER PUBLICATIONS

International Search Report and Written Opinion dated Dec. 23, 2019 from International Application No. PCT/US2019/050658.

*Primary Examiner* — George Manuel
(74) *Attorney, Agent, or Firm* — Beyer Law Group LLP

(57) ABSTRACT

Neural network based heart rhythm classifiers are described. The neural network is configured to receive an electrocardiogram segment and to output an indication of whether the electrocardiogram segment represents a heart rhythm that is suitable for treatment by a defibrillation shock. Preferably, the received electrocardiogram segment is not transformed or processed prior to its reception by the neural network and no features of the electrocardiogram are identified to the neural network. In some embodiments, the received electrocardiogram segment is the sole input to the neural network. In various embodiments, the neural network is configured to classify electrocardiogram segments obtained while CPR was being performed on the patient. Classifiers that output a characteristic of CPR are also described. Such outputs may include an indication of whether CPR was being performed while the ECG was being detected, com-
(Continued)

pression depth, etc. The described classifiers are well suited for use in defibrillators.

25 Claims, 5 Drawing Sheets

Related U.S. Application Data

(60) Provisional application No. 62/731,255, filed on Sep. 14, 2018.

(51) Int. Cl.
| | | |
|---|---|---|
| *A61B 5/361* | (2021.01) | |
| *G06N 3/045* | (2023.01) | |
| *A61B 5/346* | (2021.01) | |
| *A61B 5/366* | (2021.01) | |

(52) U.S. Cl.
CPC .......... *A61N 1/3904* (2017.08); *G06N 3/045* (2023.01); *A61B 5/366* (2021.01); *A61N 1/3987* (2013.01)

(58) Field of Classification Search
CPC .. A61B 5/7264; A61B 5/7267; A61N 1/3904; A61N 1/3956; A61N 1/3987; G06N 3/045; G06N 3/084; G16H 50/70
See application file for complete search history.

(56) References Cited

U.S. PATENT DOCUMENTS

| | | | |
|---|---|---|---|
| 5,819,007 | A | 10/1998 | Elghazzawi et al. |
| 6,192,273 | B1 | 2/2001 | Igel et al. |
| 6,304,773 | B1 | 10/2001 | Taylor et al. |
| 6,430,435 | B1 | 8/2002 | Hsu et al. |
| 6,658,290 | B1 | 12/2003 | Lin et al. |
| 6,961,611 | B2 | 11/2005 | Dupelle |
| 7,797,043 | B1 | 9/2010 | Dupelle et al. |
| 7,996,073 | B2 | 8/2011 | Busche et al. |
| 8,064,995 | B1 | 11/2011 | Dupelle et al. |
| 8,145,307 | B2 | 3/2012 | Zhang et al. |
| 8,160,698 | B2 | 4/2012 | Elghazzawi et al. |
| 8,335,559 | B2 | 12/2012 | Tan et al. |
| 8,744,573 | B2 | 6/2014 | Freeman |
| 8,903,490 | B2 | 12/2014 | Li |
| 9,002,443 | B2 | 4/2015 | Zhang et al. |
| 9,126,055 | B2 | 9/2015 | Abdeen et al. |
| 9,144,390 | B2 | 9/2015 | Amann |
| 9,409,034 | B2 | 8/2016 | Babaeizadeh et al. |
| 9,443,141 | B2 | 9/2016 | Mirowski et al. |
| 9,597,524 | B2 | 3/2017 | Jorgenson et al. |
| 9,724,008 | B2 | 8/2017 | Sullivan et al. |
| 9,795,799 | B2 | 10/2017 | Powers |
| 9,839,368 | B2 | 12/2017 | Tan et al. |
| 9,919,160 | B2 | 3/2018 | Firoozabadi et al. |
| 10,112,054 | B2 | 10/2018 | Beyer et al. |
| 10,123,741 | B2 | 11/2018 | Wang et al. |
| 10,124,183 | B2 | 11/2018 | Snyder |
| 10,136,826 | B2 | 11/2018 | Sullivan et al. |
| 2007/0213775 | A1 | 9/2007 | Snyder |
| 2008/0103403 | A1 | 5/2008 | Cohen et al. |
| 2008/0208070 | A1 | 8/2008 | Snyder et al. |
| 2012/0245648 | A1 | 9/2012 | Elghazzawi et al. |
| 2014/0361983 | A1 | 12/2014 | Dolfing et al. |
| 2016/0133160 | A1* | 5/2016 | Packer ............... A61B 5/308 600/595 |
| 2016/0296762 | A1 | 10/2016 | Ramachandran et al. |
| 2016/0331260 | A1 | 11/2016 | Han et al. |
| 2017/0112401 | A1 | 4/2017 | Rapin et al. |
| 2017/0319080 | A1 | 11/2017 | Albert |
| 2017/0361118 | A1 | 12/2017 | Liu et al. |
| 2017/0361119 | A1 | 12/2017 | Gehman et al. |
| 2017/0361120 | A1 | 12/2017 | Liu et al. |
| 2017/0361121 | A1 | 12/2017 | Liu et al. |
| 2018/0116537 | A1 | 5/2018 | Sullivan et al. |
| 2018/0160983 | A1 | 6/2018 | Galloway et al. |
| 2018/0233227 | A1 | 8/2018 | Galloway et al. |
| 2018/0260706 | A1 | 9/2018 | Galloway et al. |
| 2018/0333104 | A1 | 11/2018 | Sitek |
| 2018/0350468 | A1 | 12/2018 | Friedman et al. |
| 2019/0001144 | A1 | 1/2019 | Liu et al. |
| 2019/0038907 | A1 | 2/2019 | Snyder |
| 2019/0046113 | A1 | 2/2019 | Nikolic |
| 2020/0085333 | A1 | 3/2020 | Freed et al. |

FOREIGN PATENT DOCUMENTS

| | | |
|---|---|---|
| WO | WO 2017/072250 | 5/2017 |
| WO | WO 2017/167891 | 10/2017 |
| WO | WO 2017/220328 | 12/2017 |
| WO | WO 2017/220353 | 12/2017 |
| WO | WO 2018/119316 | 6/2018 |
| WO | WO 2018/148690 | 8/2018 |

* cited by examiner

SHOCKABLE HEART RHYTHM CLASSIFIER FOR DEFIBRILLATORS

CROSS REFERENCE TO RELATED APPLICATIONS

This application is a Continuation of U.S. application Ser. No. 16/568,030, which claims the priority of U.S. Provisional Patent Application No. 62/731,255 filed Sep. 14, 2018, both of which are incorporated herein by reference in their entirety.

BACKGROUND

The present invention relates generally to systems for automatically classifying cardiac rhythms to determine whether a patient has a heart rhythm that is appropriate for defibrillation shock therapy.

Defibrillators are devices that apply electric shock therapy to cardiac patients experiencing abnormal heart rhythms that may be treated by defibrillation shock therapy. There are several types of defibrillators that are currently available. External defibrillators are most commonly used in emergency situations in which a patient has suffered cardiac arrest, or where a cardiac arrest is imminent. External defibrillators include automated external defibrillators (AEDs) and manual defibrillators. Manual defibrillators are generally intended to be operated by trained emergency medical personnel or physicians and typically give the operator a great deal of control over the administration of a defibrillation shock. AEDs are typically designed to be used by lay operator and therefore automate most or all of the defibrillators functionality, including cardiac rhythm diagnosis and deciding whether or not a defibrillation shock should be delivered. If the AED is fully automated, the AED will deliver the defibrillation shock without requiring any input commands from a user. In contrast, when the AED is partially automated, the AED will typically inform an operator that a shock is advised, but will require that the operator push a "shock" button in order to initiate the defibrillation shock. Internal (implanted) defibrillators are implanted into the chests of patients that are known to have cardiac issues that cannot be treated in other ways. Internal defibrillators typically operate in an automatic mode.

Regardless of their type, defibrillators typically include electrocardiogram (ECG) detection circuitry configured to obtain and output an ECG signal from electrodes connected to a patient. For external defibrillators such as AEDs, the electrodes typically take the form of pads or paddles placed on the patient's chests. For implantable defibrillators, the electrodes are connected internally—as for example by attachment directly to a patient's heart or at other locations deemed appropriate for defibrillation. The ECG signal outputted by the ECG detection circuitry is then typically processed in various ways and thereafter passed to a rhythm detector or classifier which determines whether the patient has a shockable heart rhythm. If a shockable rhythm is detected, the AED will deliver a defibrillation shock to the patient.

The two most common conditions treated by defibrillation shock therapy are Pulseless Ventricular tachycardia (aka VT or V-Tach) and Ventricular fibrillation (VF or V-Fib). The classifiers must be able to accurately identify the presence of these types of rhythms as well as a variety of less common cardiac rhythms that can benefit from a defibrillation shock. Just as importantly, they must be able to distinguish normal rhythms and abnormal rhythms such as normal sinus rhythm, atrial fibrillation, sinus blockage, supraventricular tachycardia, idioventricular contraction, premature ventricular contraction, and asystole for which defibrillation shocks are not advised.

Over the years a number of electrocardiogram classification schemes have been proposed and implemented for use in identifying shockable rhythms A few such classification methods include frequency domain analysis, gradient pattern detection, waveform shape matching techniques and neural networks. One common classification approach is to identify (extract) selected features of the QRS portions of an ECG signal and to base classification on those features. As understood by those familiar with reading electrocardiograms, the recurring spikes in a ventricular waveform from an electrocardiogram are known as the R waves. The Q and S waves respectively, are the smaller inverted spikes on either side of an R wave. Typical QRS features of interest might include parameters such as QRS width, amplitude, polarity, area, r-r interval, etc. These extracted features are submitted to a classifier which classifies the heart signal based on the extracted features. The classification results are then used to determine whether the detected cardiac rhythm is a good candidate for defibrillation shock therapy.

Although the existing classifiers work well, there are continuing efforts to further improve the accuracy of detection.

SUMMARY

A variety of neural network based shockable heart rhythm classifiers are described. The neural network is configured to receive an electrocardiogram segment as an input and to generate an output indicative of whether the received electrocardiogram segment represents a heart rhythm that is suitable for treatment by a defibrillation shock. Preferably, the received electrocardiogram segment is not transformed or processed prior to its reception by the neural network and no features of the electrocardiogram are identified to the neural network. In some embodiments, the received electrocardiogram segment is the sole input to the neural network. In some embodiments the classifier is trained to identify shockable heart rhythms in electrocardiogram segments obtained while a patient is receiving cardio-pulmonary resuscitation.

In some embodiments, the neural network has an input, at least two hidden layers and an output layer. The input may be a raw detected electrocardiogram segment. In some embodiments, the input is received as an array of samples obtained at a sampling frequency in the range of 100 to 600 samples per second on an electrocardiogram segment having a length of less than 15 seconds.

In some embodiments, the convolutional neural network includes in the range of 2-6 hidden layers. In some embodiments, each hidden layer includes in the range of 8 to 32 filters. In some embodiments, each filter has a filter size in the range of 3-16 and a stride rate in the range of 1-5.

In some embodiments, the output of the classifier is a numeric probability value indicative of a determined probability that the received electrocardiogram segment represents a heart rhythm that is suitable for treatment by a defibrillation shock.

In another aspect, neural network based classifiers that output a parameter indicative of CPR are described. The neural network is configured to receive an electrocardiogram segment as an input and to generate an output parameter indicative of CPR performed on the patient. Preferably, the received electrocardiogram segment is not transformed or processed prior to its reception by the neural network and no features of the electrocardiogram are identified to the neural network. In some embodiments, the received electrocardiogram segment is the sole input to the neural network. In some embodiments the classifier is trained to identify shockable heart rhythms in electrocardiogram segments obtained while a patient is receiving cardio-pulmonary resuscitation.

In some embodiment, the output classification is or includes an indication of whether CPR was being performed on the patient during detection of the electrocardiogram segment. In some embodiments, the output classification is or includes a parameter indicative of CPR compression depth or compression rate. In some embodiments, the classifier is further configured to output a second classification indicative of whether the received electrocardiogram segment represents a heart rhythm that is suitable for treatment by a defibrillation shock.

In various embodiments, the neural network shockable rhythm classifier is incorporated into a defibrillator capable of delivering defibrillation shock therapy. In some embodiments the defibrillator is configured to provide one or more instruction(s) or feedback to a user based at least in part on the output classification.

In various embodiments, the instruction(s) or feedback include one or more of: an instruction to stop or begin CPR compressions; an instruction to push harder or reduce the pressure during CPR compressions; or an instruction to increase or decrease the frequency of CPR compressions.

Methods of training the described neural networks are also described.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION OF THE PREFERRED EMBODIMENTS

Figure 1A:
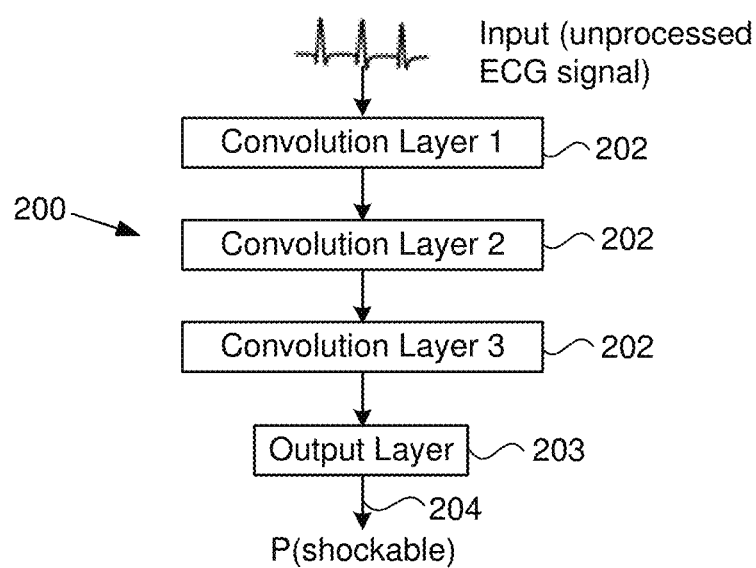
FIGS. 1(a) and 1(b) are block diagrams illustrating a convolutional neural network based shockable rhythm classifier in accordance with one embodiment.

The present invention relates generally to a neural network shockable rhythm classifier that is configured to identify cardiac rhythms that are suitable for defibrillation shock therapy. The described classifier is well suited for use in defibrillators to identify shockable heart rhythms in real time. Referring next to FIG. 1(a), a shockable rhythm classifier 200 in accordance with one embodiment will be described. The classifier 200 is convolutional neural network based classifier. In the illustrated embodiment the neural network includes an input layer 201, three convolutional neural net hidden layers 202 and an output layer 203.

In other embodiments, more or fewer convolutional (hidden) layers may be used. Minimally a single hidden layer may be used—although typically, a minimum of two or three hidden layers is preferred. Typically is it not desirable to provide too many layers so that the model does not simply memorize examples instead of actually learning useful features about the data. Additionally, there is a point where adding more layers may provide trivially small improvements such that extra computation is not justified. Therefore, in general, two to six convolutional layers are believed to work well.

In the embodiment illustrated in FIG. 1(a), the sole input to the classifier 200 is a segment of an ECG signal having a designated length. The output of the classifier is a weight or a set of weights indicating the classifier's confidence level that the inputted segment constitutes a shockable rhythm. This output is sometimes referred to herein as shock classification 204. The designated length of the ECG segment analyzed may vary based on the needs of the system used. In general, the ECG segment length should be long enough so that the segment can be reliably analyzed, but short enough so that analysis is not unduly delayed. This is important because defibrillators are typically used in life saving situations and extended delays in obtaining or processing the ECG signals that are analyzed can delay the administration of a shock when needed, which can adversely impact the probability of defibrillation being successful. In some embodiments, ECG segment lengths on the order of 4 to 15 seconds long are used although in different embodiments either shorter or longer segments may be used. By way of example, in some specific implementations, ECG segments less than 10 seconds long, as for example, four (4) to eight (8) second long ECG segments have been found to work well.

Figure 1B:
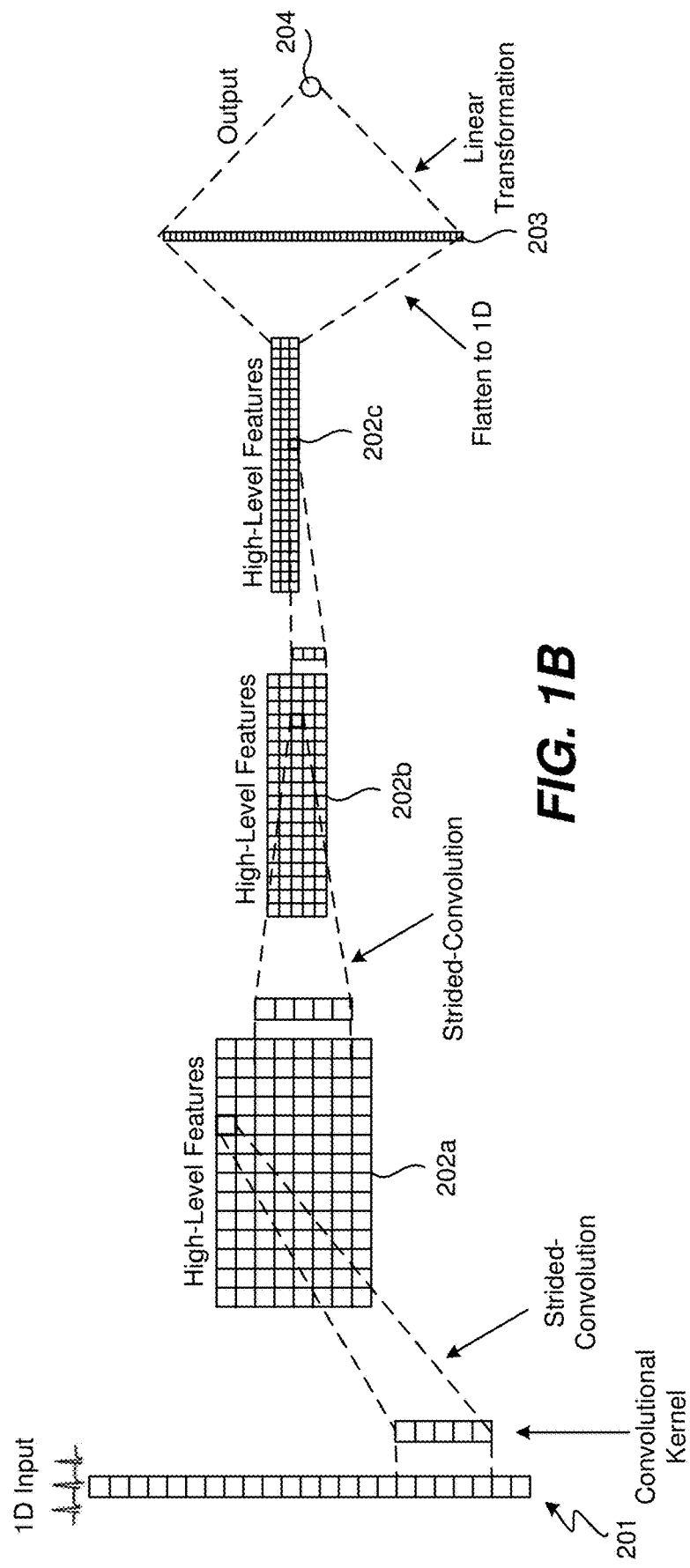

FIG. 1(b) is another diagrammatic illustration of the shockable rhythm classifier 200 which highlights the nature of the input layer and the convolutional nature of the hidden layers 202(a), 202(b) and 202(c). In the illustrated embodiment, the input is a 1-dimensional vector. More specifically, the input may take the form of a linear array of ECG samples corresponding to the designated segment length.

The specific sample rate used may vary, but sample rates on the order of 100 to 600 samples per second are believed to be suitable. The value of each sample may correspond to the amplitude of the ECG signal in the corresponding sample period—as for example in millivolts. The total number of samples in the input array is the product of the sample rate (samples/sec) times the segment length (seconds).

In each convolutional layer 202, a convolutional kernel is strided over the previous layer or set of high-level features, which can be understood as a sliding-window that applies a dot-product between the input and the kernel. After each layer is computed, the next layer contains a set of high-level features that represent patterns and combinations of patterns that were found by the convolutional kernels. A convolutional kernel represents a pattern and if a matching pattern is found in the input, then the dot-product will return a higher value, thus passing that information on to the next layer to form a high-level feature. The last convolutional layer output is flattened into a 1 dimensional vector 203. And finally a linear transformation is applied to each of the values in the flattened layer and the final scalar value 204 is the outputted value. The outputted value may be a value between 0 and 1, where a value greater than or equal a designated threshold represents a shockable input signal and a value less than the designated threshold represents a non-shockable input signal.

A noteworthy feature of the classifier 200 is that it is purely data driven based on raw ECG segments that have not undergone typical analysis such as wavelet analysis, beat to beat analysis, or QRS detection analysis. It should be appreciated that the ECG samples will often have gone through some relatively minimal level of signal filtering by the ECG sensing circuitry to reduce noise (e.g. low or high pass filters), etc. but no ECG feature extraction. That is, the input to the classifier is a segment of the ECG signal outputted by ECG sensing circuitry itself (which is sometimes referred to herein as the raw or unprocessed ECG signal). No effort is made to extract features of the ECG prior to classification, and/or to utilize such extracted features as inputs to the classifier as has often been done in prior art classifiers, including prior art neural network based classifiers (e.g., wavelet transforms). Similarly, no effort is made to transform the ECG signal prior to submission to the classifier as is common in a variety of other prior art classifiers, including some prior art neural network based classifiers.

Although feature extraction and/or signal transformation can be useful for many prior art classifiers, we believe that better classification results can be attained using a deep learning neural network that is trained based on raw or minimally processed ECG segments. This is because, as a practical matter, extracted features cannot fully define a rhythm as complex as an ECG of a patient experiencing an arrhythmia or tachycardia. Similarly, as a practical matter, any signal transformation will inherently result in the loss of some information carried in the original signal—which inherently limits the performance of a classifier. Therefore, a classifier that takes in an unprocessed signal can theoretically achieve equal or better performance than one that has had processing done prior to being fed to the classification module. Modern deep learning based neural networks such as the described convolutional neural network are well suited for handling complex inputs and the complexities of an raw ECG signal are well within the capabilities of modern deep machine learning tools. Furthermore, as discussed in more detail below, the use of the raw or substantially unprocessed ECG signal allows the classifier to analyze the ECG segments for characteristics of interest that are not part of conventional arrhythmia classification such as patient gender, age or other patient properties that may be reflected in the ECG but may be obscured or lost in the pre-processing required by conventional classifiers.

It is noted that many ECG detection circuits do some minimal level of filtering of the ECG signal to reduce noise. The output of such ECG detection circuits is considered to be an unprocessed/raw ECG signal in the context of this disclosure.

The neural network classifier 200 is generated using deep machine learning trained with error back propagation. As will be appreciated by those familiar with machine learning, it is generally desirable to train the classifier with a training set having a large number of samples including a number of samples of each type of rhythm that the classifier might be expected to encounter and classify. The training data set preferably includes a large number of each type of rhythm of interest including normal rhythms, unusual rhythms of different types that are not shockable rhythms, and every type of rhythm for which defibrillation shock therapy is desired. In general, the quality of the classifier's results will improve when larger training sets are used that include a large number of samples of each rhythm type of interest. An advantageous feature of neural network based classifiers is that as more training data becomes available, the classifier can be updated by retraining to incorporate the most recent information available.

The segments utilized in training have the same segment length as the segments that will be analyzed by the classifier and the training segments are input in the same format as the samples that will be analyzed. Thus, the training segments are inputted as an array of samples that are sampled at a designated sampling rate and correspond to the designated sample length.

The training of the neural network classifier is automated in that the neural network trains itself based on the data it receives and the back propagation of errors identified in the training. The automated training defines the set of weights attributed to each link between nodes. The classifier is trained using raw ECG segments that are the same length as the segments to be handled by the classifier. For example, if 8 second segments are to be used as the inputs to the classifier, then the training is based on 8 second segments (although as mentioned above, the actual segment length used may vary in accordance with the design goals and needs of any particular implementation). Each of the segments used in training is known to correspond to either a shockable rhythm or a rhythm that is not suitable for treatment by administering a defibrillation shock. The back propagation of errors identified during the training is particularly helpful to establishing a robust and highly accurate model.

The neural network classifier 200 may be created by any appropriate neural network generator—as for example, TensorFlow™ which is an open source machine learning framework and software library originally developed and made publically available by Google. Classifiers created using TensorFlow™ are well suited for use in handling the described unprocessed/raw ECG signal.

As will be appreciated by those familiar with convolutional neural networks, a good way to specify a convolutional neural network layer is to specify the number of convolutional layers, the number of filters, the filter (kernel) size and the stride rate. The specific values for the number of convolutional layers, filters, filter size and stride rate may vary widely based on the needs of any particular system. For example, it is believed that in the range of 2 to 6 convolutional layers having on the order of 8-32 filters, filter sizes on the order of 3-16 and a stride rate in the range of 1-5 are generally suitable for defibrillation heart rhythm classification. Of course, these values are somewhat dependent on one another.

As previously mentioned, the input to the convolutional neural network may be a linear array of ECG samples. The specific sample rate used may vary, but sample rates on the order of 100 to 600 samples per second as for example 250 samples per second are believed to be suitable.

In the first described embodiment, the output of the classifier 200 is simply a value indicative of whether the received ECG reflects a cardiac rhythm that the classifier believes can be treated by defibrillation shock therapy. The outputted value may be a simple shock/no shock decision, or it may be a numeric probability value indicative of the probability that the detected rhythm is a shockable rhythm. When the output of the classifier is a numeric probability value, the defibrillator controller may have a defined threshold probability which if met or exceeded, is treated as a shockable rhythm.

In some embodiments, the classifier does not output an identification of the specific type of shockable rhythm that is detected (e.g., no effort is made to identify whether the detected shockable rhythm was V-Tach or V-Fib or some other type of shockable rhythms) For an AED, this is often sufficient because the AED itself only needs to know whether or not a shock should be delivered and a diagnosis of the particular type of rhythm detected is less important—especially if the detected electrocardiogram is stored so that it can be presented or transmitted to emergency and/or medical personnel who can analyze the ECG itself.

In other embodiments, it may be helpful for the classifier to also output a diagnosis of the type of rhythms detected. This can readily be done by reconfiguring the output layer of the neural network appropriately. For example, the classifier can readily be configured and trained to output a classification of the analyzed rhythm (e.g., normal, V-Tach, V-Fib, etc.) in addition to, or in place of the simple shock decision. Again, the output can be characterized in terms of a numeric probability instead of simply the classification if/when desired. The probability associated with the analyzed rhythm diagnosis can be helpful to both (a) responding and/or treating medical personnel as an indicator of the patient's condition; and (b) to facilitate analysis of the efficacy of the defibrillator or the classifier itself and potentially to help facilitate future training of the classifier.

Figure 2:
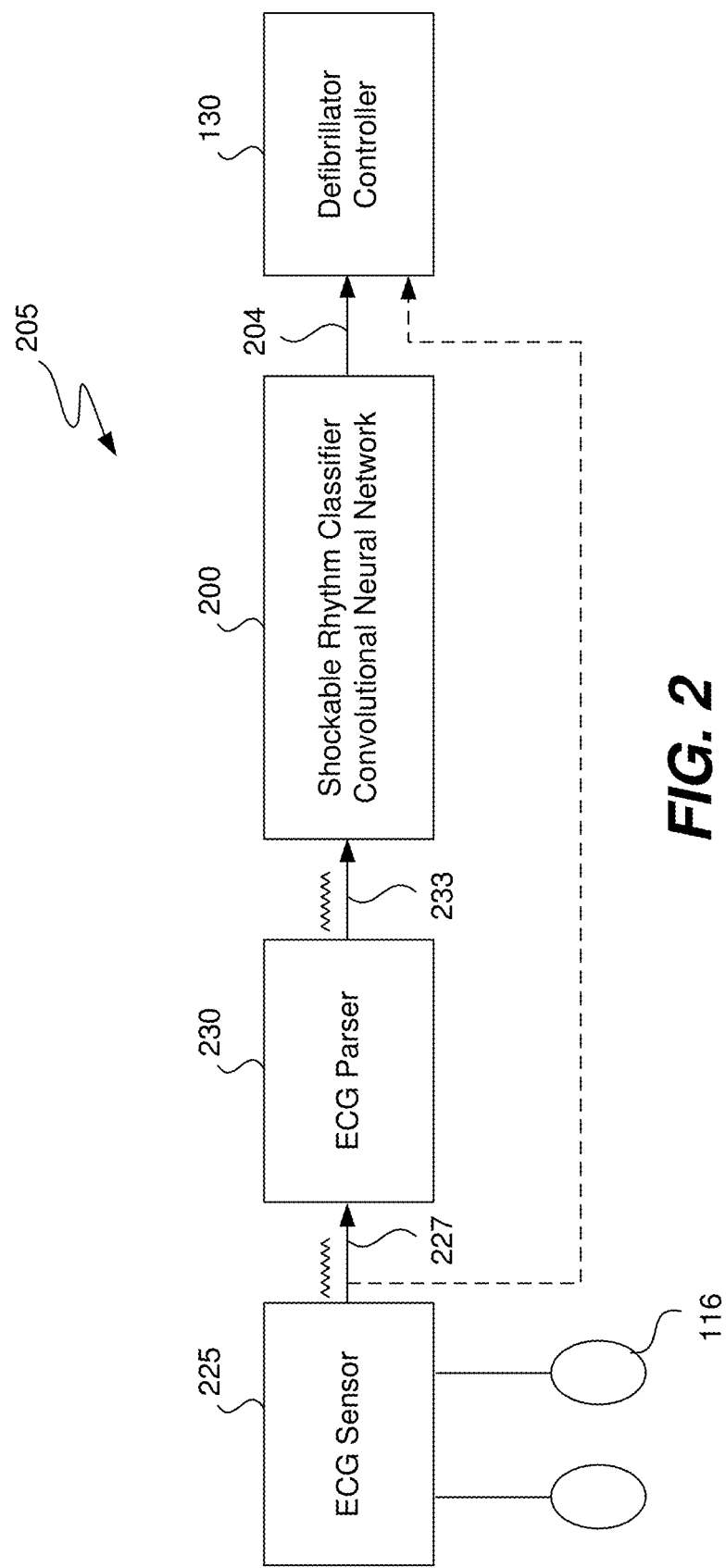
FIG. 2 is a block diagram of an ECG sensing and classifying system that incorporates a neural network based shockable rhythm classifier.

Referring next to FIG. 2, an ECG handling system 205 will be described. The ECG handling system 205 includes an ECG sensor/detector 225, electrodes 116, ECG parser 230 and convolutional neural network based shockable rhythm classifier 200. The ECG sensor 225 is arranged to detect electrical cardiac signals picked up by electrodes 116 and to output an electrocardiogram signal 227 in a conventional manner. The ECG sensor/detector 225 typically does some basic filtering, but is intended to output a standard ECG signal—which is sometimes referred to herein as an unprocessed/raw ECG signal. That is, the sensor/detector 225 does not do any special processing, feature extraction, or transformation of the ECG signal.

It should be appreciated that the basic ECG sensor/detector output filtering commonly includes some low pass filtering; high pass filtering; DC offset filtering; and/or notch filtering. The high and low pass filtering are designed to eliminate noise in frequency ranges outside of frequencies relevant to the ECG itself (i.e. above and below relevant ECG frequencies). The DC offset filtering is intended to normalize the signal around a designated reference (e.g., a mean of 0 mV as opposed to a mean of 3 mV). The notch filter is intended to filter out expected noise—as for example filtering out the 50 Hz or 60 Hz noise that exists in AC power supplies in Europe and the United States respectively). As will be appreciated by those familiar with the art, all of these would be considered good practice filtering of the output of an ECG sensor/detector and are not designed to extract or highlight any features or characteristics of the ECG signal itself. As mentioned above, the unprocessed/raw ECG signal utilized as the input to the classifier will typically have been subjected to this type of basic ECG sensor/detector output filtering.

The electrodes 116 may take the form of any electrodes suitable for detecting a patient's ECG. For example, in the context of an AED, the electrodes 116 may be standard external defibrillator electrode pads or paddles. In the context of an implanted defibrillator, the electrodes 116 may take the form of conventional internal defibrillator electrode leads.

The electrocardiogram signal 227 is fed to ECG parser 230 which forwards appropriate length segments 233 of the electrocardiogram signal 227 to the shockable rhythm classifier 200 as described above. In some embodiments, the parser 230 is arranged to forward ECG segments 233 to the shockable rhythm classifier at regular intervals. The specific intervals at which updates are sent may be widely varied to meet the needs and capabilities of any particular implementation. By way of example, update intervals on the order of 0.1 to 2 seconds work well in many implementations, although either longer or shorter update intervals may be appropriate for specific implementations. Thus, for example, if 8 second long segments are sent the classifier every 0.2 seconds, each sample sent by the parser 230 would contain the last eight seconds of ECG signal. In this way, the ECG segment sent to the classifier is effectively indexed 0.2 seconds each sample. For each sample, the shockable rhythm classifier identifies whether the sample is perceived to represent a shockable rhythm and that determination (shock classification 204) may be sent to a defibrillator controller 130 which takes the appropriate actions based on the current circumstances, including the shock classification determined by shockable rhythm classifier 200.

It is noted that the classifier can continue to monitor the ECG rhythm and report its analysis even after a shock decision has been made by the defibrillator controller. Therefore, if there is a sudden change in the ECG after a shock decision has been made but before a shock is actually delivered (e.g., a change from V-Fib to a normal sinus rhythm (NSR)), then the defibrillator controller can decide not to deliver a shock.

Figure 3:
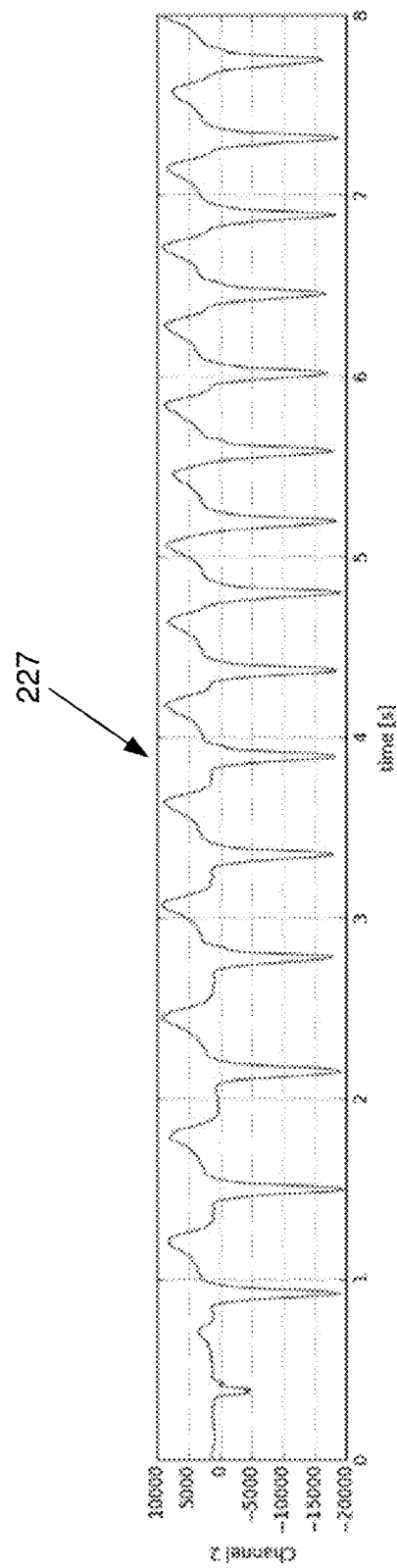
FIG. 3 is a timing diagram showing an ECG segment suitable for use by the convolutional neural network based shockable rhythm classifier of FIGS. 1(a) and 1(b).

An example of a shifted, real time series of ECG segments passed from the parser to the classifier 200 is illustrated in FIG. 3. FIG. 3 shows an ECG reading 227 at a given time. The parser 230 takes the last 8 seconds of the ECG signal and passes that segment, to the shockable rhythm classifier. After a designated interval (e.g. 0.2 seconds), another sample will be sent to the classifier. Through the delay, the ECG sensor continues to detect and output more of the ECG. When it is time to send the next sample, the parser will send the last 8 seconds of the EGG segment that it then has. This process is repeated as long as classification is desired and the system keeps receiving usable ECG signal. When the sample interval is short compared to the sample length, the majority of the signal sent to the classifier will be overlapping with the addition of the portion of the ECG signal that has been received since the last sample and the truncation of the portion of the ECG signal that is older than the sample length.

The described shockable rhythm classifier may be incorporated into a defibrillator of any type—including automated external defibrillators (AEDs), manual external defibrillators, wearable defibrillators, implantable defibrillators, etc. By way of example, a couple specific AED designs that can benefit from the described shockable rhythm classifier are described in applicant's U.S. Pat. No. 10,029,109 filed Dec. 7, 2017 and patent application No. 62/674,711 filed May 22, 2018 and Ser. No. 16/145,657 file Sep. 28, 2018, each of which is incorporated herein by reference. Of course, the described shockable rhythm classifier may be incorporated into a wide variety of other defibrillator designs as well.

In many embodiments, the defibrillator will store the entire detected ECG signal either persistently or transitorily. The stored ECG can be provided to responding emergency personnel and/or medical personnel to provide a better understanding of the incident.

The shockable rhythm classifier and associated ECG handling may also be implemented in a wide variety of different manners. In some embodiments, the classifier may be implemented on a dedicated neural network processor (NNP), such as Google's Tensor Processing Unit (TPU) or Intel's Neural Network Processor. In other embodiments, the shockable rhythm classifier may be implemented in or as a software module executed on a processor or microcontroller such as defibrillator controller 130. The functionality of the ECG parser may also be performed by the neural network processor, of if preferred, the defibrillator controller. In other embodiments, parser 230 and/or the shockable rhythm classifier 200 may be implemented as one or more separate components having its/their own processor(s). In still other embodiments, the shockable rhythm classifier and/or the parser 230 may be implanted in discrete or programmable logic as may be appropriate for any particular implementation.

Figure 4:
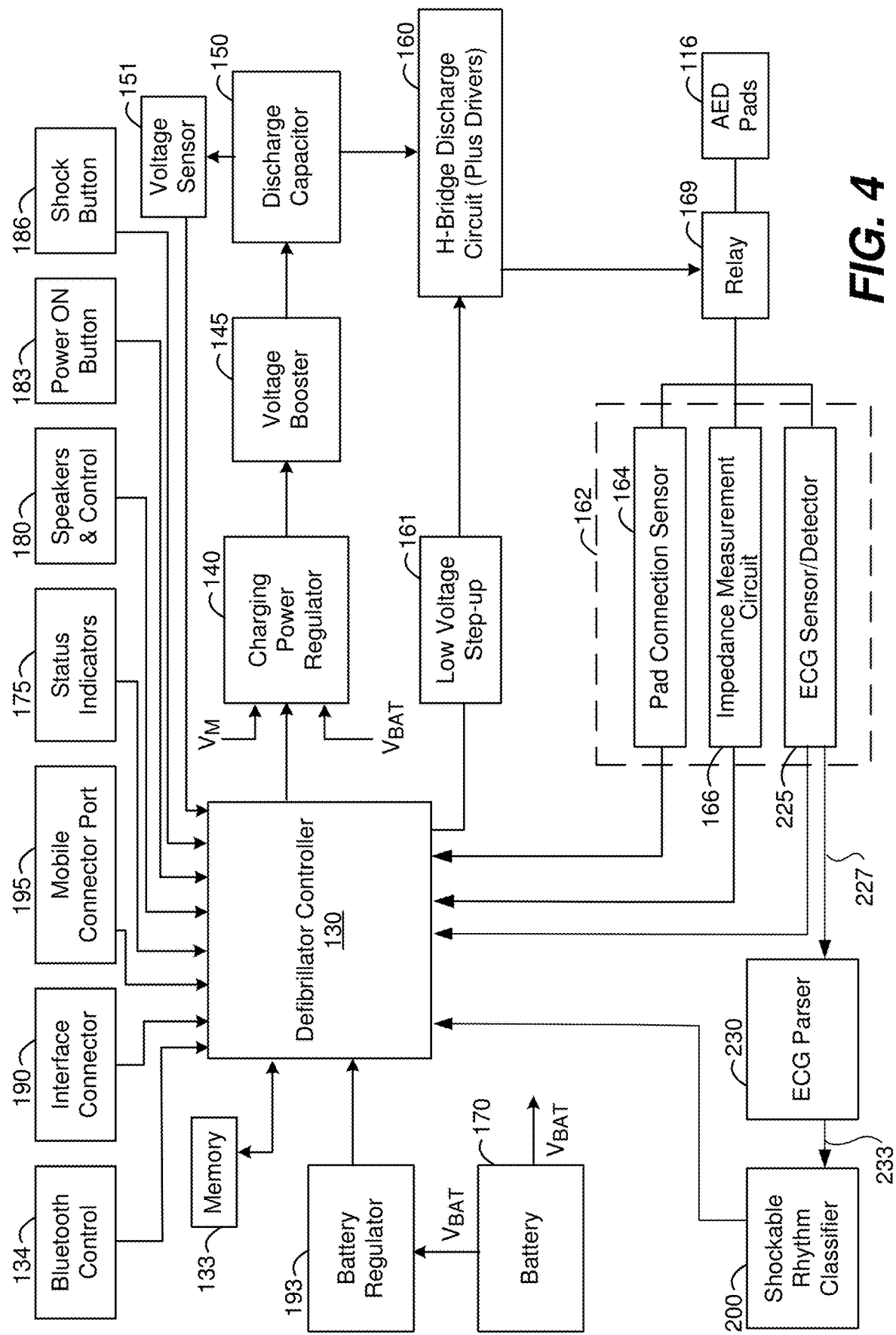
FIG. 4 is a block diagram of an electronics architecture of an automated external defibrillator (AED) that incorporates an ECG sensing and classifying system.

FIG. 4 is an electrical block diagram illustrating an automated external defibrillator architecture that incorporates the described ECG handling mechanism 205. In the illustrated embodiment, the electrical components of defibrillator unit 110 include a defibrillator controller 130, memory 133, a charging power regulator 140, a voltage booster 145 (which may have multiple stages), a high voltage capacitor 150 for temporarily storing sufficient electrical energy suitable to provide a defibrillation shock, discharge control circuitry 160, pad related sensing circuitry 162 and relays 169, power storage unit 170, battery regulator 193, status indicator(s) 175, speaker(s) 180, shockable rhythm classifier 200 and one or more electrical connectors (e.g., interface connector 190, mobile connector port 195, charger connector 197, etc). The charging power regulator 143 and voltage booster 145 which cooperate to control the charging of the shock discharge capacitor 150, are sometimes referred to herein as a charging circuit.

The defibrillator controller 130 is configured to control the operation of the base defibrillator unit and to direct communications with external devices, as appropriate. In some embodiments, the defibrillator controller includes a processor arranged to execute software or firmware having programmed instructions for controlling the operation of the base unit, directing interactions with a user and communications with external components. As suggested above, in some embodiments, the ECG parser and the shockable rhythm classifier 200 may take the form of software modules executed on such a processor.

The defibrillator unit 110 may optionally be configured so that it is capable of drawing power from certain other available power sources beyond power storage unit 170 to expedite the charging of shock discharge capacitor 150. The charging power regulator 140 is configured to manage the current draws that supply the voltage booster, regardless of where that power may originate from. For example, in some embodiments, supplemental power may be supplied from a mobile device coupled to mobile connector port 195 or from a portable charger/supplemental battery pack coupled to charger connector 197.

The voltage booster 145 is arranged to boost the voltage from the operational voltage of power storage unit 170 to the desired operational voltage of the discharge capacitor 150, which in the described embodiment may be on the order of approximately 1400V-2000V (although the defibrillator may be designed to attain any desired voltage). In some embodiments, the boost is accomplished in a single stage, whereas in other embodiments, a multi stage boost converter is used. A few representative boost converters are described in the incorporated '835 patent application. By way of example, in some embodiments, a flyback converter, as for example, a valley switching flyback converter may be used as the voltage booster 145—although it should be appreciated that in other embodiments, a wide variety of other types of voltage boosters can be used.

A voltage sensor 151 is provided to read the voltage of the capacitor 150. The voltage sensor 151 may take the form of a voltage divider or any other suitable form. This capacitor voltage reading is utilized to determine when the shock discharge capacitor 150 is charged suitably for use. The sensed voltage is provided to controller 130 which determines when the capacitor 150 is charged sufficiently to deliver a defibrillation shock. The capacitor 150 can be charged to any desired level. This can be useful because different defibrillation protocols advise different voltage and/or energy level shocks for different conditions. Furthermore, if the initial shock is not sufficient to restart a normal cardiac rhythm, some recommended treatment protocols call for the use of progressively stronger impulses in subsequently administered shocks (up to a point).

The discharge circuitry 160 may take a wide variety of different forms. In some embodiments, the discharge circuitry 160 includes an H-bridge along with the drivers that drive the H-bridge switches. The drivers are directed by defibrillator controller 130. The H-bridge outputs a biphasic (or other multi-phasic) shock to patient electrode pads 116 through relays 169. The relays 169 are configured to switch between an ECG detection mode in which the patient electrode pads 116 are coupled to the pad related sensing circuitry 162, and a shock delivery mode in which the patient electrode pads 116 are connected to H-Bridge to facilitate delivery of a defibrillation shock to the patient. Although specific components are described, it should be appreciated that their respective functionalities may be provided by a variety of other circuits.

The pad related sensing circuitry 162 may include a variety of different functions. By way of example, this may optionally include a pad connection sensor 164, an impedance measurement filter 166, and ECG sensor/detector circuitry 225. The pad connection sensor is arranged to detect the pads are actually connected to (plugged into) the base defibrillator unit 110. The ECG sensor/detector circuitry 225 senses electrical activity of the patient's heart when the pads are attached to a patient and outputs the electrocardiogram signal 227 to the shockable rhythm classifier 200 (via parser 230) for analysis to determine whether the detected cardiac rhythm indicates a condition that is a candidate to be treated by the administration of an electrical shock (i.e., whether the rhythm is a shockable rhythm) and the nature of the recommended shock. When the shockable rhythm classifier 200 is not integrated with the defibrillator controller 130, the electrocardiogram signal 227 may also be passed to the defibrillator controller 130 which stores the detected rhythm in memory so that it can be shown or sent to emergency medical personnel if/when desired. When a shockable rhythm is detected, the controller 130 directs the user appropriately and controls the shock delivery by directing the H-bridge drivers appropriately.

In some embodiments, the power storage unit 170 takes the form of one or more rechargeable batteries, although other power storage devices such as one or more supercapacitors, ultracapacitors, etc. and/or combinations thereof may be used as deemed appropriate for any particular application. In some embodiments, the defibrillator unit 110 is capable of drawing power from other available power sources for the purpose of one or both of (a) expediting the charging of shock discharge capacitor 150 and (b) recharging the power storage unit 170. In some embodiments, the battery can be recharged using one or more of the externally accessible connector ports 195, a dedicated charging station, a supplemental battery pack, an interface unit, etc. When wireless charging is supported, the base defibrillator unit may include a wireless charging module 174 configured to facilitate inductive charging of the power storage unit 170 (e.g. using an inductive charging station, or other devices that support inductive charging, as for example an inductively charging battery pack, a cell phone with inductive charging capabilities, etc.).

The defibrillator unit 110 also includes a number of software or firmware control algorithms installed in memory 133 and executable on the defibrillator controller 130. The control algorithms have programmed instructions suitable for controlling operation of the defibrillator and for coordinating communications between the defibrillator unit 110 and any connected or remote devices 105. These control routines include (but are not limited to): capacitor charge management algorithms for managing the charging of the discharge capacitor; capacitor discharge management algorithms for managing the delivery of a shock as necessary; user interface management algorithms for managing the user instructions given by the defibrillator and/or any connected user interface devices during an emergency; battery charge control algorithms for managing the charging of power storage unit 170 and routing charging power to other connected components; testing and reporting algorithms for managing and reporting self-testing of the base unit; software update control algorithms and verification files that facilitate software updates and the verification of the same. When the shockable rhythm classifier 200 and parser 225 are implemented algorithmically, the control algorithms can also include those modules.

CPR Artifacts

AEDs are typically used when it is suspected that a person might be experiencing cardiac arrest. Cardiac arrest treatment protocols typically call for defibrillation in conjunction with CPR to revive the patient. An issue encountered by many existing external defibrillator is that they cannot reliably classify ECGs that are obtained while CPR is being performed because the CPR compressions distort the detected ECG signals significantly. Therefore, many AEDs instruct the rescuer to stop CPR for a period to allow the defibrillator to analyze the patient's heart rhythm to facilitate the determination of whether a defibrillation shock is advised.

In some embodiments, the neural network classifier 200 is trained using only "clean" ECG segments that do not have any CPR artifacts (i.e., were not obtained while CPR was being performed). If such a classifier is used in an AED or other defibrillator expected to be used in emergency situations where CPR might be expected, it may be desirable to instruct the user to stop CPR for a brief period to attain a clean ECG signal to be used by the classifier, much like most current defibrillators do.

In other embodiments, the neural network classifier 200 may be trained to identify shockable rhythms that are detected while CPR is being performed. This can readily be accomplished by including a large variety of different types of ECG segments that were obtained while CPR was being performed in addition to using clean ECG segments as in the previous embodiments. This can be a powerful enhancement since it doesn't require a user to stop giving CPR as appropriate while the classifier 200 determines whether the patient has a shockable rhythm. A challenge to training the classifier in this manner is the lack of public available data sets for training that categorize rhythms obtained while CPR was being performed. However, as more such data becomes available, the classifier can be trained (and retrained) to identify shockable rhythms regardless of whether CPR is being performed while obtaining the ECG signal.

CPR Compression Feedback

As discussed above, CPR is typically recommended in conjunction with defibrillation as a preferred treatment for cardiac arrest. Therefore, many AEDs include prompts to encourage responders to perform CPR and/or instructions regarding how to perform CPR. Given the importance of CPR, some AEDs go so far as to include a chest compression detector (typically accelerometer based) attachment that can detect chest compression. The detected chest compressions can then be analyzed and appropriate feedback can be given to the user (e.g., press harder, reduce pressure, compress at a slower or faster rate, etc.).

In some embodiments, the neural network shockable rhythm classifier 200 or a parallel neural network CPR classifier (not shown) can be trained to also provide indications about the depth or efficacy of chest compression, and/or the rate of, CPR compressions. Such information can be used by the AEDs processor to provide real time feedback to the user about any chest compressions being administered. This information can be used for other purposes as well. For example, if the AED knows that a rescuer is touching the patient, it may defer shock delivery until the rescuer takes their hand of the patient to avid inadvertently shocking the rescuer.

Other Types of Classification

It has been demonstrated in the literature that there are some variations in ECG readings associated with some particular arrhythmias that vary in accordance with the patient's gender. Knowledge of the patient's gender can be useful in a variety of applications including: facilitating the generation of gender tailored operator instructions; when reporting the incident to first responders and/or medical personnel; potentially tailoring the shock treatment itself; etc. An advantage of using the unprocessed/raw ECG samples is that in some embodiments, with the availability of sufficient ECG samples for training, the classifier can be trained to report a prediction of the patient's gender, along with a confidence level associated with the prediction. That gender prediction can then be used by the defibrillator controller in any manner deemed appropriate.

One potential use case for using gender information is in tailoring the user instructions in gender relevant manners. For example, recommended defibrillation practices often call for the removal of all clothing over the chest and the defibrillator may issue an audio prompt and/or display instructions instructing a user to remove all clothing over the patient's chest. Studies have shown that AED users that are not medically trained are often reluctant to remove the bra of female patients for cultural reasons, which can hinder the efficacy of the device. When the gender of the patient is known or suspected by the device to be female, the clothing removal prompt can be modified to emphasize that if the patient is wearing a bra, the bra should be removed as well.

In another example, if the detected ECG suggests that the patient is male (or that the patient is more likely to have a relatively hairy chest), the user instructions may be modified to emphasize that if the patient has a hairy chest, it is important to shave the regions where the electrode pads are applied.

The recommended shock protocol can also vary with the age/size of the patient. For example, it is well established that pediatric patients respond better to lower energy defibrillation shocks as compared with adult patients (E.g. 150 J shocks for adult vs. 50 J shocks for pediatric). A challenge encountered by current AEDs is distinguishing patient age and size before delivering defibrillation therapy. Current defibrillators rely upon the operator (who may be a bystander responding to the SCA incident) to decide whether the patient is classified as pediatric (e.g., under 8 years old or under 55 lbs) by either selecting pediatric defibrillation electrode pads which attenuate the shock to be a lower energy shock, or by pressing a button or otherwise indicating that the patient is a child. Requiring an untrained operator to decide whether a patient should be treated as a pediatric patient vs. an adult increases the risk of misclassification of the patient.

An advantage of using the unprocessed/raw ECG samples is that in some embodiments, with the availability of sufficient ECG samples for training, the classifier can be trained to report a prediction of the patient's age and/or size, along with a confidence level associated with the prediction. That age/size prediction can then be used by the defibrillator controller in any manner deemed appropriate. For example, if the classifier has confidence that the patient qualifies for treatment as a pediatric patient, the defibrillator controller can prompt the user to utilize pediatric pads if the patient is a child to insert the appropriate electrode pads, or perform other actions particular to a pediatric patient, for instance performing lower compression CPR. With high enough confidence, the classifier output could also be used by the defibrillator controller to adjust the energy of the defibrillation shock depending on the inferred patient properties. For instance if the classifier was 90% confident that the patient was under 55 lbs and under 8 years of age, the defibrillator could automatically reduce the defibrillation shock from say 150 J to 50 J, and further instruct the user to place the electrode pads according to proper pediatric patient, and further perform CPR in accordance with pediatric CPR instead of adult CPR.

Other Features

Although only a few embodiments of the invention have been described in detail, it should be appreciated that the invention may be implemented in many other forms without departing from the spirit or scope of the invention. Therefore, the present embodiments should be considered illustrative and not restrictive and the invention is not to be limited to the details given herein, but may be modified within the scope and equivalents of the appended claims.

What is claimed is:

1. A shockable heart rhythm classifier comprising a neural network trained to identify shockable cardiac rhythms, the shockable heart rhythm classifier being configured to receive a detected electrocardiogram segment as an input and to generate an output classification indicative of whether the received electrocardiogram segment represents a heart rhythm that is suitable for treatment by a defibrillation shock, wherein the received electrocardiogram segment contains CPR artifacts indicative of cardio-pulmonary resuscitation (CPR) being performed during the detection of the electrocardiogram segment.

2. A shockable heart rhythm classifier as recited in claim 1 wherein the neural network is a convolutional neural network.

3. A shockable heart rhythm classifier as recited in claim 2 wherein the convolutional neural network has in the range of two to six convolutional layers.

4. A shockable heart rhythm classifier as recited in claim 3 wherein each layer includes in the range of 8 to 32 filters.

5. A shockable heart rhythm classifier as recited in claim 4 wherein each filter has a filter size in the range of 3-16 and a stride rate in the range of 1-5.

6. A shockable heart rhythm classifier as recited in claim 1 wherein the received electrocardiogram segment is a raw electrocardiogram segment.

7. A shockable heart rhythm classifier as recited in claim 6 wherein the raw electrocardiogram segment is the sole input to the neural network.

8. A shockable heart rhythm classifier as recited in claim 1 wherein no features of the received electrocardiogram are identified to the neural network.

9. A shockable heart rhythm classifier as recited in claim 1 wherein the received electrocardiogram segment is an array of samples obtained at a sampling frequency in the range of 100 to 600 samples per second and having a length of less than 15 seconds.

10. An automated external defibrillator (AED) comprising a shockable heart rhythm classifier as recited in claim 1, the AED unit further comprising:
a capacitor unit capable of temporarily storing and discharging sufficient energy to deliver a defibrillation shock to a patient via electrode pads configured to be attached to a patient;
shock delivery circuitry for discharging the capacitor unit to deliver the defibrillation shock;
defibrillation electrode pads;
electrocardiogram circuitry for detecting electrocardiogram segment via the defibrillation electrode pads when the defibrillation electrode pads are attached to a patient.

11. A shockable heart rhythm classifier as recited in claim 1, wherein the neural network is further trained to identify shockable cardiac rhythms based on electrocardiogram segments that do not contain CPR artifacts.

12. A heart rhythm classifier comprising a neural network trained to identify shockable cardiac rhythms, the heart rhythm classifier being configured to:
receive a patient's detected electrocardiogram segment as an input;
generate Drill a first output classification indicative of cardio-pulmonary resuscitation (CPR) performed on the patient while the electrocardiogram segment was being detected; and
output a second classification indicative of whether the received electrocardiogram segment represents a heart rhythm that is suitable for treatment by a defibrillation shock.

13. A heart rhythm classifier as recited in claim 12 wherein the first output classification is or includes an indication of whether CPR was being performed on the patient during detection of the electrocardiogram segment.

14. A heart rhythm classifier as recited in claim 12 wherein the first output classification is or includes a parameter indicative of CPR compression depth.

15. A heart rhythm classifier as recited in claim 12 wherein the first output classification is or includes a parameter indicative of CPR compression rate.

16. A heart rhythm classifier as recited in claim 12 wherein the neural network is further trained to identify shockable cardiac rhythms based on electrocardiogram segments that do not contain CPR artifacts indicative of CPR being performed during the detection of the electrocardiogram segment.

17. An automated external defibrillator (AED) that includes the heart rhythm classifier of claim 12, wherein the defibrillator is configured to provide an instruction or feedback to a user based at least in part on the output classification.

18. An AED as recited in claim 17 wherein the instruction or feedback includes an instruction to stop or begin CPR compressions.

19. An AED as recited in claim 17 wherein the instruction or feedback includes an instruction to push harder or reduce the pressure during CPR compressions.

20. An AED as recited in claim 17 wherein the instruction or feedback includes an instruction to increase or decrease the frequency of CPR compressions.

21. A method of training a shockable rhythm classifier comprising:

providing a neural network;

training the neural network to identify shockable cardiac rhythms using a multiplicity of electrocardiogram segments of a designated length that contain CPR artifacts as inputs, wherein each electrocardiogram segment is known to correspond to either (a) a shockable cardiac rhythm deemed to be representative of a cardiac rhythm that is suitable for treatment by administration of a defibrillation shock, or (b) a cardiac rhythm that is not deemed to be representative of a cardiac rhythm that is suitable for treatment by administration of a defibrillation shock; and as part of the training, back propagating errors that are identified during the training.

22. A method as recited in claim 21, wherein the electrocardiogram segments each have a length of less than 15 seconds and are sampled at a sampling frequency in the range of 100 to 600 samples per second.

23. A method as recited in claim 21 wherein the received electrocardiogram segments are raw electrocardiogram segments and no features of features of the electrocardiogram segments are identified to the neural network during the training.

24. A method as recited in claim 21 wherein the neural network includes at least two hidden layers and no more than six hidden layers.

25. A method as recited in claim 24 wherein each layer includes in the range of 8 to 32 filters and each filter has a filter size in the range of 3-16 and a stride rate in the range of 1-5.

* * * * *

UNITED STATES PATENT AND TRADEMARK OFFICE
CERTIFICATE OF CORRECTION

PATENT NO. : 11,903,741 B2
APPLICATION NO. : 17/364575
DATED : February 20, 2024
INVENTOR(S) : Freed et al.

It is certified that error appears in the above-identified patent and that said Letters Patent is hereby corrected as shown below:

In the Specification

1. Column 2, Line 7, insert --.-- after --rhythms--.

2. Column 7, Line 2, insert --.-- after --rhythms)--.

In the Claims

1. In Claim 12 (Column 14, Line 39), delete "Drill".

Signed and Sealed this
Seventh Day of May, 2024

Katherine Kelly Vidal
*Director of the United States Patent and Trademark Office*